(12) United States Patent
Skibo

(10) Patent No.: US 6,998,413 B1
(45) Date of Patent: Feb. 14, 2006

(54) TREATMENT OF NEOPLASMS WITH YUJUNGAMYCINS

(75) Inventor: Edward B. Skibo, Scottsdale, AZ (US)

(73) Assignee: Arizona Board of Regents acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 09/889,530

(22) PCT Filed: Jan. 26, 2000

(86) PCT No.: PCT/US00/02026

§ 371 (c)(1),
(2), (4) Date: Jul. 18, 2001

(87) PCT Pub. No.: WO00/43005

PCT Pub. Date: Jul. 20, 2000

Related U.S. Application Data

(60) Provisional application No. 60/117,199, filed on Jan. 26, 1999.

(51) Int. Cl.
*A61K 31/415* (2006.01)
*C07D 403/02* (2006.01)

(52) U.S. Cl. .................................. 514/394; 548/302.4
(58) Field of Classification Search ............... 514/394; 548/302.4
See application file for complete search history.

(56) References Cited

U.S. PATENT DOCUMENTS 5,246,955 A * 9/1993 Skibo et al. ................ 514/394

OTHER PUBLICATIONS

Skibo et al, "Studies of Pyrrolo[1,2-a]benzimidazolequinone DT-Diaphorose Substrate Activity . . .", J. Med. Chem., vol. 40, pp. 1327-1329 (1997).*

* cited by examiner

*Primary Examiner*—Frederick Krass
(74) *Attorney, Agent, or Firm*—Fennemore Craig, P.C.

(57) ABSTRACT

Yungamycin A has been demonstrated to have unexpected in vivo anticancer activity. New compounds Yungamycin B and C are also disclosed, and have been demonstrated to be specific for DT-diaphorase, as well as to have in vivo anticancer activity.

10 Claims, 2 Drawing Sheets

TREATMENT OF NEOPLASMS WITH YUJUNGAMYCINS

This Application is based on U.S. Provisional Application Ser. No. 60/117,199 filed Jan. 26, 1999 which was filed as PCT Serial Number PCT/US00/02026 on International Filing Date Jan. 26, 2000 and assigned International Publication Number WO 00/43005, which was published on Jul. 27, 2000.

Financial assistance for this project was provided by U.S. Government through the National Science Foundation under Grant Number CHE-9522640 and through the National Institutes of Health under Grant Number CA 73758; and the United States Government may own certain rights to this invention.

The present invention relates to compounds derived from the pyrrolo[1,2-a]benzimidazole ring system and the discovery of their unique and unexpected antineoplastic activity, particularly against central nervous system, ovarian, and lung cancers.

BACKGROUND OF THE INVENTION

Figure 1:
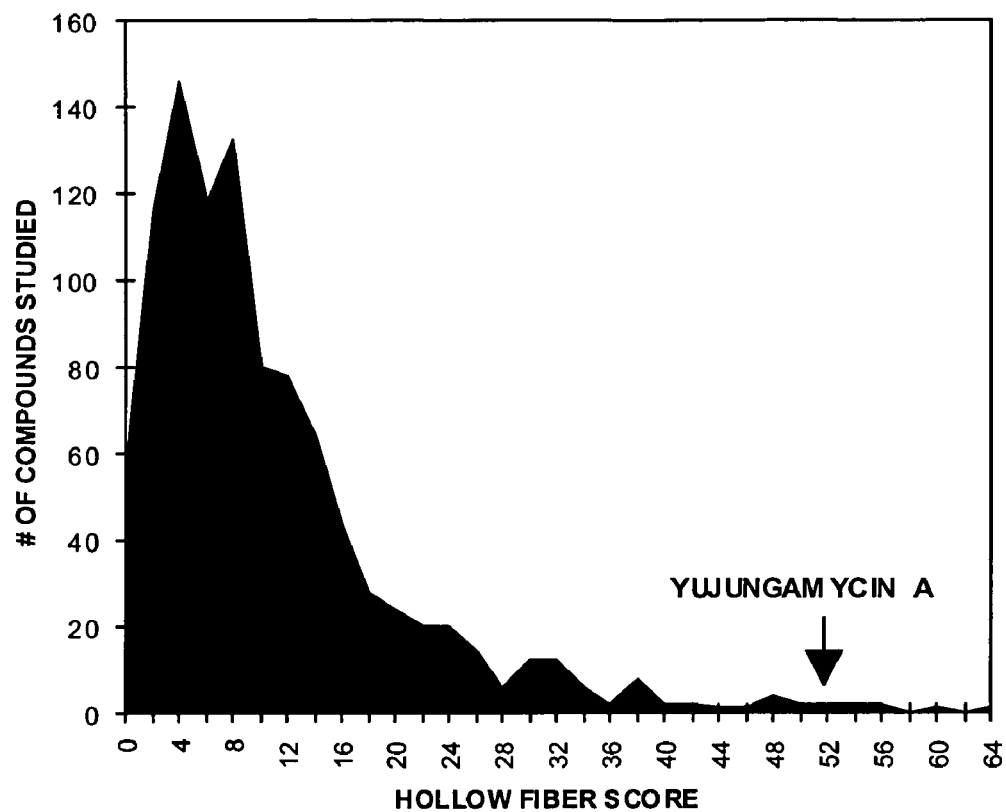
FIG. 1. illustrates a plot of a number of compounds studied at the National Cancer Institute, versus the hollow fiber score of the compounds.

Work in this laboratory has been involved with the design of a new class of DNA cleaving agent based on the pyrrolo [1,2-a]benzimidazole (PBI) ring system for some time (Skibo, E. B. and Schulz, W. G. Pyrrolo[1,2-a]benzimidazole-Based Aziridinyl Quinones. A New Class of DNA Cleaving Agent Exhibiting G and A Base Specificity. *J. A. Med. Chem.* 36: pp 3050–3055, 1993; op. cit., Schulz, Nieman and Skibo, 1995.) These agents were designed to alkylate the phosphate backbone upon reduction to create a hydrolytically-labile phosphotriester, SCHEME A. While in the reduced form, these agents can hydrogen-bond to the major groove and thereby recognize base pairs. (Skibo, E. S., Gordon, S., Bess, L., Boruah, R. and Heileman, J. Studies of Pyrrolo[1,2-a]benzimidazole Quinone DT-Diaphorase Substrate Activity, Topoisomerase II Inhibition Activity, and DNA Reductive Alkylation. *J. Med. Chem.* 40:pp 1327–1339, (1997).) The reducing enzyme DT-diaphorase can activate antitumor agents by two-electron reduction in both normal and cancerous tissues, (op. cit. Riley and Workman, 1992; Marin, A., deCerain, A. L., Hamilton, E., et al. DT-diaphorase and cytochrome B-5 reductase in human lung and breast tumors. *Br. J. Cancer Vol* 76, Iss 7: pp923–929, 1997) as illustrated in the inset of SCHEME A. Depending on the organ and species source, the substrate and inhibition properties of the enzyme can vary widely (op. cit., Rauth, Goldberg and Misra, 1997; Wu etc. 1997). This inventor maintains that since the structure of DT-diaphorase varies by organ system, the enzyme could also vary by the organ system cancer. Thus cancers originating from these organs (lung, renal, ovarian, etc.) will possess slightly different DT-diaphorase, assuming some degree of differentiation. The PBIs possess variable cytotoxicity in cell lines and a corresponding variable activity in vivo models. Therefore this inventor has conducted the synthesis and cytotoxicity/in vivo screens of both known and new PBIs.

The previously reported structure corresponding to Yujungamycin A (op. cit. Skibo, Gordon et al., (1997) possessed low cytotoxicity in cell lines. However, the present application shows that Yujungamycin A is unexpectedly active in vivo. Therefore, Yujungamycin B and C were prepared to exploit this unexpected finding.

SCHEME A

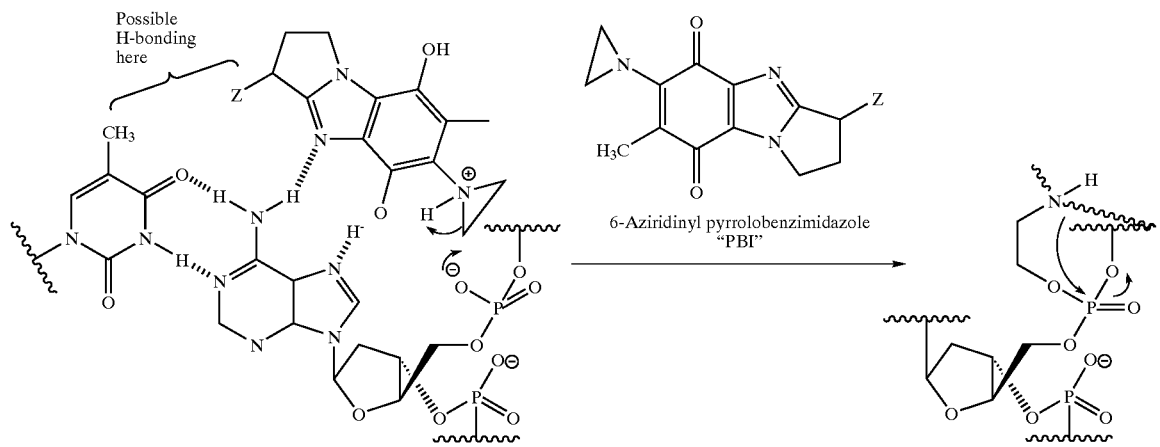

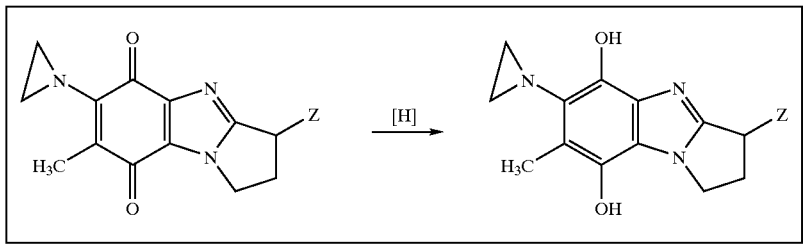

Some bulky substituents and stereochemistry (op. cit. Skibo etc. 1997) are known to influence the substrate specificity of DT-diaphorase. In the present invention both the stereochemistry and the hydrogen bonding capabilities represented by the enantiomers of yujungamycins A, B, C. were employed to influence DT-diaphorase substrate specificity.

Synthesis

The preparation of the yujungamycins is outlined in Schemes 1 and 2.

Previous synthetic studies led to the preparation of racemic 4 employing 1 and either racemic or S(−) 3. (op cit Skibo etc. 1997; Skibo, E. B., Islam, I., Schulz, W. G., Zhou, R., Bess, L. and Boruah, R. The Organic Chemistry of the Pyrrolo[1,2-a]benzimidazole Antitumor Agents. An Example of Rational Drug Design. Synlett pp 297–309, (1996); Skibo, E. B. Pyrrolobenzimidazoles in cancer treatment. Expert. Opin. Ther. Patents. Vol 8, Iss 6:pp 673–701, (1998)). Acetylation of S(−) 4 to S(−) 5 was followed by conversion to yujungamycin A(−), which is the S enantiomer, Scheme 1. The previously unknown R(+) enantiomer was prepared from racemic 4 employing an acyltransferase (ALTUS 20 CLEC catalyst), which afforded R(+) 5 as the major product. Altus Inc. provides a kit of 40 acyltransferases to screen for enantiomeric excesses, only the mentioned acyltransferase gave a suitable result. Conversion of R(+) 5 to the R(+) form of yujungamycin A was carried out as previously described (op. cit., Skibo etc. 1997).

In order to prepare the R(+) or the S(−) forms of yujungamycin B and C, the R(+) or S(−) forms of 4 were trifluoroacetylated to afford 7, Scheme 2. The trifluoroacetyl group was easily removed after the bromination and nitration reactions to afford the common intermediate 9. Yujungamycin B was prepared from 9 by reduction, Fremy oxidation, and finally aziridination as previously described for the PBIs. (op. cit., Skibo etc. 1996) The same procedure was employed to convert the 3-carbamido derivative 10 to yujungamycin C.

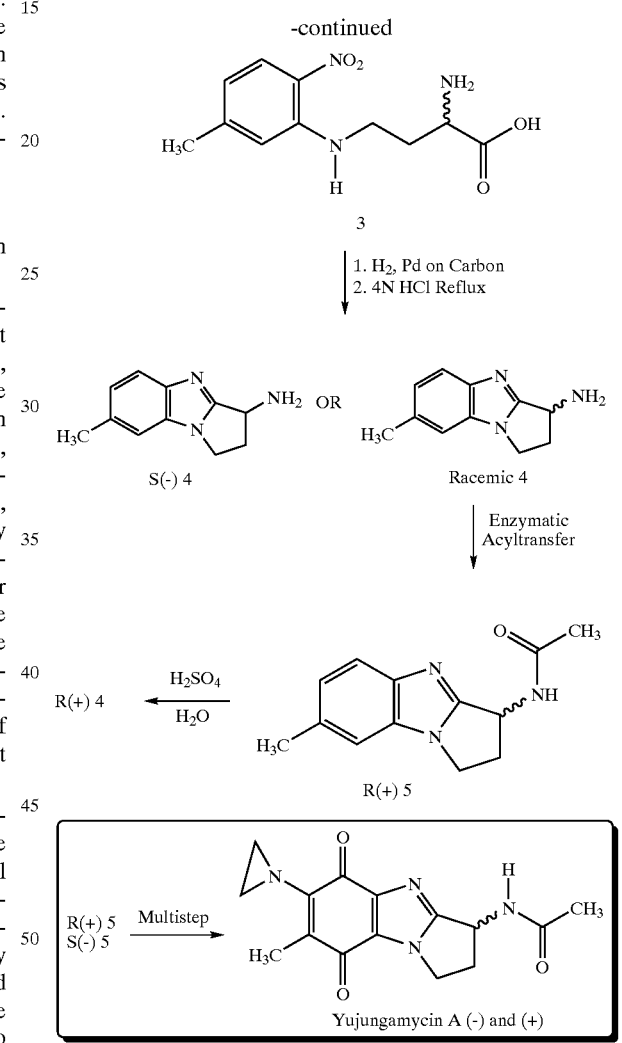

SCHEME 1

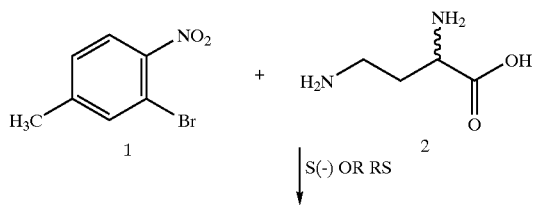

SCHEME 2

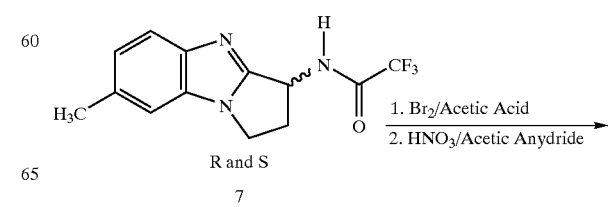

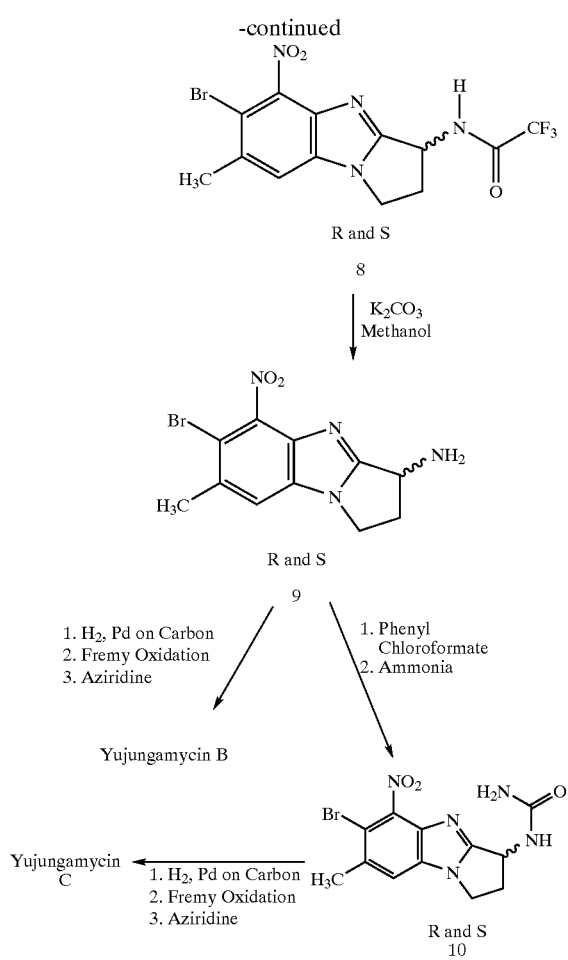

Antitumor Activity

Figure 2:
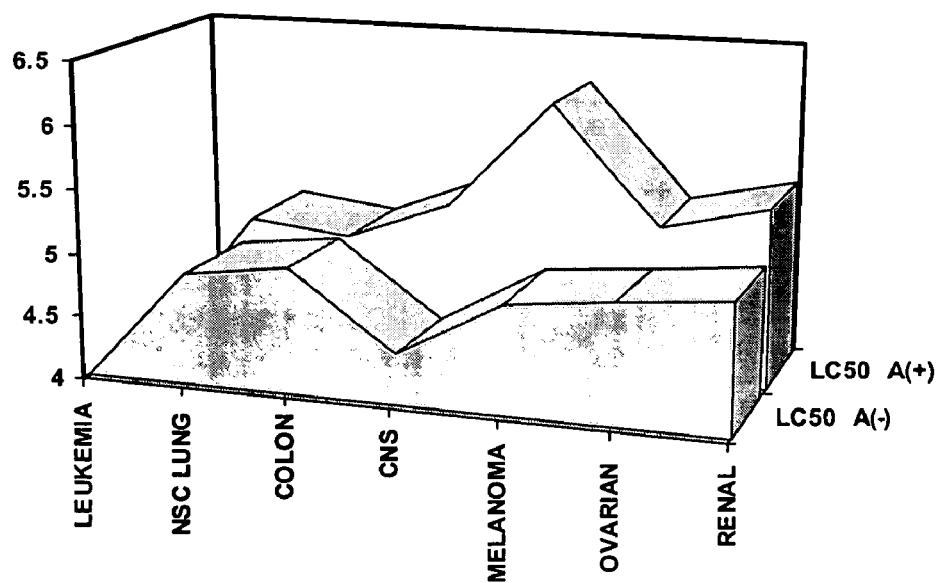
FIG. 2. illustrates the plots of average $-\log LC_{50}$ values versus the cancer type for yujungamycin A(+) and A(-). Each $-\log LC_{50}$ value is the average of up to eight values.

In vivo screening results of Yujungamycin A, employing the new hollow fiber assay, are discussed in conjunction with SCHEME B and FIGS. 1 and 2.

Hollow fiber assays are carried out in the following way. Human tumor cells are cultivated in polyvinylidene fluoride hollow fibers, and a sample of each cell line is implanted into each of two physiological compartments (intraperitoneally and subcutaneously). Mice are treated with either a high or a low dose using a QD×4 schedule (four daily treatments) administered intraperitoneally. Altogether, twelve cell lines are studied resulting in 48 possible test combinations (12 cell lines×2 sites×2 doses). A score of two is given to each test in which there is a % T/C of 50 or less (tumor mass 50% or less than the control. Thus the highest possible score is a 96, but the typical score is only 5 and the highest score achieved is a 64. Typically the score is broken down into a intraperitoneal (IP) and a subcutaneous (SC) score. A good SC score ($\geq 8$) indicates that the drug is able to get to the tumor site (subcutaneous) from a distant site (intraperitoneal) of injection. Both PBI-A and PBI-B shown in Table 1 are active in the hollow fiber assay and are active against melanoma, NSC lung cancer, breast cancer, and ovarian cancer. These compounds are covered by two patents. (Skibo, E. B. and Islam, I. Synthesis and Elucidation of Azamitosene and Iminoazamitosene. U.S. Pat. No. 5,015, 742 1991; Skibo, E. B., Islam, I. and Alberts, D. S., Antineoplastic Agents and Methods of Using the Same. U.S. Pat. No. 5,246,955, 1993).

The three substituent of the PBI is crucial of cytotoxic activity, but is not required for the actual reductive alkylation process (requires the aziridinylquinone). The 3-unsubstituted PBI and the 3-hydroxy PBI are devoid of activity while the lipophilic 3-propanoate derivative showed animal toxicity (100% drug deaths) at doses as low as 5 mg/kg without any significant antitumor activity. The acetate and the carbamate, PBI-A and PBI-B respectively, appear to have a suitable balance of polarity and lipophilicity in the 3-substituent for antitumor activity. These findings prompted the investigation of the yujungamycins, all of which bear a nitrogen bound to the 3-position. The resulting acetamido, amino, or carbamido substituents are more stable to hydrolysis than the corresponding oxygen derivatives (PBI-A and PBI-B). Therefore it was postulated that the yujungamycins would be more cytotoxic than the PBIs. The interaction of these substituents with DT-diaphorase would contribute to the selective cytotoxicity of these agents. Indeed, the data in SCHEME B shows that yujungamycin A(−) did obtain a higher score than the PBIs. The high subcutaneous score of 14 indicated that this agent can kill cancer cells at a location distant from the site of injection.

SCHEME B

| | Intraperitonal Score | Subcutaneous Score | Total Score | |
|---|---|---|---|---|
| PBI-A | 40 | 8 | 48 | Cancer cell line types sensitive to the PBis: Melanoma, Non-Small Cell Lung Cancer, Breast Cancer, Ovarian Cancer |

SCHEME B-continued

| | Intraperitonal Score | Subcutaneous Score | Total Score | |
|---|---|---|---|---|
| PBI-B | 24 | 6 | 30 | Cancer cell line types sensitive to A(+):<br>Non-Small Cell Lung Cancer<br>CNS Cancer<br>Ovarian Cancer |
| Yujungamycin A (−) | 38 | 14 | 52 | |

The National Cancer Institute has tested hundreds of new compounds, either synthetic or natural products, in the hollow fiber screen. (Hollingshead, M., Plowman, J., Alley, M., Mayo, J. and Sausville, E. Relevance of Tumor Models in Anticancer Drug Development. In: *Contributions to Oncology*, Germany: Krager Verlag, 1998). These compounds are active in vitro and therefore chosen for the in vivo hollow fiber assay. FIG. 1 shows the position of yujungamycin A(−) among the compounds screened at the National Cancer Institute. The typical antitumor agent only has a hollow fiber score of ~5, while yujungamycin A(−) scores at 52 making it one of the most active compounds studied by the National Cancer Institute.

The −log $LC_{50}$ data in FIG. 2 confirmed the prediction that selective cytotoxicity would be exhibited by the yujungamycins. Thus, yujungamycin A(+) shows substantially higher cytotoxicity against melanoma than the (−) enantiomer. However, the magnitude of the cytotoxicity (highest −$logLC_{50}$ only 6) is much less than the previously studied PBIs. (op. cit., Skibo, 1998). The extraordinary in vivo activity exhibited by yujungamycin A(−) was entirely unexpected. If cell line data is an indication of relative activity, then the more active A(+) enantiomer should be even more effective in vivo.

Figure 3:
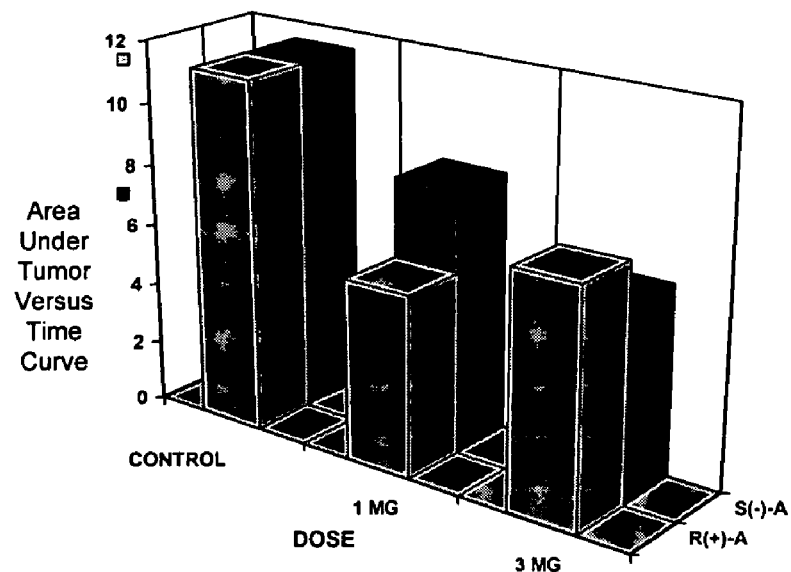
FIG. 3. illustrates the results of S(-) and R(+) Yujungamycin A in the B-16 melanoma model in C57/bl mice. These compounds were studied at two dose levels: 1 and 3 mg/Kg IP on days 1, 5, and 9 after tumor implantation into the front flank muscle. Shown in the bar graph is the area under the tumor versus time curve plotted against dose for each enantiomer. Note that there are no apparent differences between the enantiomers in these data.

The results of human melanoma tumor syngraft studies with R(+) and S(−) Yujungamycin A, FIG. 3, failed to show much difference in activity between the enantiomers. Although it should be pointed out that the enantiomeric differences apparent in FIG. 2 reflect the average of several cell lines for each cancer category. Perhaps the enantiomeric differences will become apparent when more syngraft studies are carried out. However, the activity of S(−)-Yujungamycin A in the syngraft assay distinguishes it from other compounds with high hollow fiber assay scores. Close inspection of FIG. 1 shows that there are a few compounds with higher scores than S(−)-Yujungamycin A, the highest score being 64 for a natural product. Many of these compounds are too toxic and do not show activity in vivo.

Figure 4:
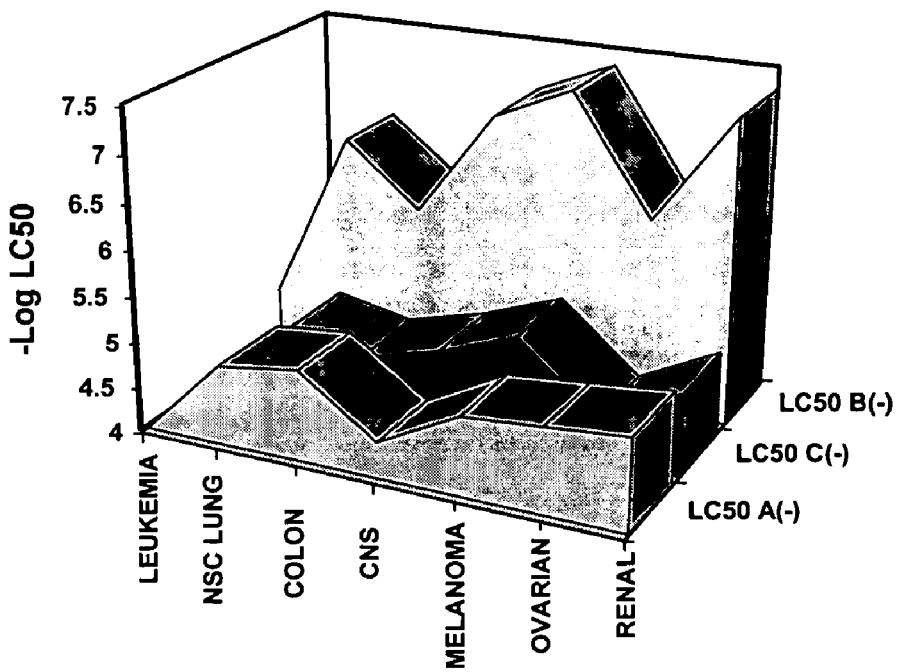
FIG. 4. illustrates the plots of $-\text{Log } LC_{50}$ versus cancer type for S(-)-1, 2, 3. Each cancer type represents the average of six to eight different cancer cell lines. The 3-amino derivative 2 shows high cytotoxicity against non-small-cell lung, central nervous system, melanoma, ovarian, and renal cancers.

Besides studying the influence of stereochemistry, the hydrogen bonding capabilities of the 3-substituent was also varied. The properties of the 3-substituent are crucial for antitumor activity with low toxicity. Extremes include the 3-hydroxy derivative, which is nearly devoid of cytotoxicity, and the 3-propanoate, which is very cytotoxic but too toxic for in vivo use. FIG. 1 shows the increasing activity in the hollow fiber assay as the 3-substituent is changed from carbamate (PBI-B), to acetate (PBI-A), and finally to 3-acetamido (Yujungamycin A). When the 3-hydroxy group is changed to 3-amino (Yujungamycin B), there is ~million-fold change in cytotoxicity. This finding suggests that a basic group in the 3-position is required for cytotoxicity, since the large difference in cytotoxicity seems to reflect the relative pKa values of a protonated amine versus a protonated alcohol. FIG. 4 contrasts the relative cytotoxicities of the S(−) forms of Yujungamycins A, B, C against several types of cancer. The high potency of Yujungamycin B, compared to the others, illustrates the importance of 3-substituent basicity on cytotoxicity. Preliminary studies indicate the 3-amino substituent greatly enhances the alkylation of DNA, perhaps explaining the high cytotoxicity.

Experimental Section (R)-(+)-3-Trifluoroacetamido-2,3-dihydro-7-methyl-1H-pyrrolo[1,2-a]benzimidazole (R(+) 7) was prepared from racemic 4 by the following three-step process.

To 543 mg (2.9 mmol) of racemic 4 in a 250 mL round bottom flask was added 310 mg of ALTUS 20 CLEC catalyst along with 104 mL of ethyl acetate. The resulting mixture was stirred vigorously for 30 min and solids were filtered off and washed 3× with 10 mL portions of $CHCl_3$. The extraction solvent was removed under reduced pressure to afford a residue, which was placed on a silica gel column employing 3% methanol in chloroform as the eluent. Pure R(+) 5 eluted from the column as the first band. The product was recrystallized from ethyl acetate/hexane: 244 mg (37%) yield; mp 219–220; TLC (chloroform/methanol [90:10] $R_f$=0.38; IR (KBr pellet) 3245, 3068, 2990, 1635, 1560, 1420 $cm^{-1}$; $^1H$ NMR ($CDCl_3$)δ 7.75 (1H, s, acetamido proton) 7.47 (1H, d, J=8.4 Hz, 5-aromatic proton), 7.02 (1H, d, J=8.4 Hz, 6-aromatic proton), 6.88 (1H, s, 8-aromatic proton), 5.41 (1H, m, 3-methine proton), 4.0–3.8 (2H, m, 1-methylene protons), 3.25–3.15 (1H, m, 2-methylene proton), 2.55–2.39 (1H, m, 2-methylene proton) 2.43 (3H, s, methyl), 2.09 (3H, s, methyl); mass spectrum (EI) m/z: 229

($M^+$), 186 ($M^+$—$COCH_3$), 171, 158, 145, 133, 116, 104. Rotations: (R)-(+) $[\alpha]_D^{25}$=+104.4° (C=0.41, MeOH).

The deacetylation of R-(+) 5 was carried out by dissolving 210 mg (0.877 mmol) in 12 mL of 1.2N hydrochloric acid and refluxing the solution for 9 h. The solvent was removed under vacuum to afford a white solid, which was dissolved in water and then buffered to pH 7 with saturated sodium bicarbonate solution. The neutralized solution was extracted 5× with 30 mL portions of chloroform and the extracts dried over sodium sulfate. Concentration of the dried extracts and recrystallization from chloroform/hexane afforded 155 mg (95%) of R(+) 4 as a white solid. Rotations: R(+) 4 $[\alpha]_D^{25}$=+20.9° (C=1.1, MeOH) and S(−) 4 $[\alpha]_D^{25}$=−20.7° (C=0.2, MeOH).

Trifluoroacetylation of R(+)$_4$ was carried out by dissolving 155 mg (0.83 mmol) in 3 mL of trifluoroacetic acid followed by addition of 3 mL of trifluoroacetic anhydride. The reaction mixture was stirred for 20 min at room temperature and then poured into 150 mL of 0.1M pH 7.0 phosphate buffer. The resulting solution was extracted 3× with 20 mL portions of ethyl acetate and the extracts were washed 2× with 10 mL portions of saturated sodium bicarbonate and then dried over sodium sulfate. The extracts were concentrated to a residue, which was recrystallized from ethyl acetate/hexane to afford 152 mg (65%) yield of R(+)-7. Rotation: (R)-(+) $[\alpha]_D^{25}$=+101.2° (C=0.55, MeOH). Anal. ($C_{13}H_{12}F_3N_3O$) C, H, O.

(S)-(−)-3-trifluoroacetamido-2,3-dihydro-7-methyl-1H-pyrrolo[1,2-a]benzimidazole (S(−) 7). To a mixture of 683 mg (3.05 mmol) of S(−) 4 was dissolved in 20 mL triflouroacetic acid. To this mixture was added 20 mL trifluoroacetic anhydride and the reaction was stirred for 25 min at room temperature. The completed reaction was poured into 700 mL of 0.1 M pH 7.0 phosphate buffer. This solution was extracted 4× with 40 mL portions of ethyl acetate and then the extracts were washed 3× with 20 mL portions of saturated aqueous bicarbonate solution and dried over $Na_2SO_4$. The solvent was removed under reduced pressure and the product recrystallized from ethyl acetate/hexane: 546 mg (63%) yield; mp 227–228° C.; TLC (chloroform/methanol [90:10]$R_f$=0.68; IR (KBr pellet) 3178, 2987, 2912, 2858, 1724, 1572, 1523, 1213, 1186, 1153 cm$^{-1}$; $^1$H NMR (CDCl$_3$) δ 9.75 (1H, bs, —NH), 7.41 (1H, d, J=8.1 Hz, 5-aromatic proton) 7.02 (1H, d, J=8.1 Hz, 6-aromatic proton), 6.79 (1H, s, 8-aromatic proton), 5.43 (1H, q, J=6.3 Hz, 3-methine proton), 4.08–3.89 (2H, m, 1-methylene proton), 3.31–3.89 (1H, m, 2-methylene proton), 2.69–2.58 (1H, m, 2-methylene proton), 2.41 (3H, s, 2-methyl protons); mass spectrum (EI mode) m/z 283($M^+$), 186 ($M^+$—$CF_3CO$), 121, 131, 105. Rotation: S(−) 7$[\alpha]_D^{25}$=−108.7° (C=0.42, MeOH). Anal. ($C_{13}H_{12}F_3N_3O$) C, H, O.

6-Bromo-3-trifluoroacetamido-2,3-dihydro-7-methyl-5-nitro-1H-pyrrolo[1,2-α]benzimidazole (8) was prepared by the following two-step procedure starting with 7:

To a solution of 500 mg (1.76 mmol) of 7 in 25 mL of acetic acid was added 0.25 mL of a solution of bromine 0.8 M in acetic acid. The resulting solution was stirred at room temperature for 20 min and then quenched by dilution with 500 mL of 0.1 M pH 7.0 phosphate buffer. The resulting mixture was extracted 3× with 80 mL portions of ethyl acetate and then the extracts were washed 2× with 80 mL portions of saturated aqueous sodium bicarbonate solution. The extracts were dried over $Na_2SO_4$ and the solvent removed under reduced pressure to afford the bromo derivative which was recrystallized from ethyl acetate/hexane: 546 mg(85%) yield: m.p. 215–217° C.; TLC (chloroform/methanol[90:10]) $R_f$=0.50; IR(KBr pellet) 3178, 2984, 2859, 1730, 1570, 1522, 1445, 1221, 1186, 1148 cm$^{-1}$; $^1$HNMR (CDCl$_3$) δ9.9 (1H, bs, amide NH), 7.61 (1H, s, 5-aromatic proton), 6.83 (1H, s, 8-aromatic proton), 5.48–5.40 (1H, m, 3-methine proton), 4.17–3.95 (2H, m, 1-methylene protons), 3.33–3.26 (1H, m, 2-methylene proton), 2.77–2.65 (1H m, 2-methylene proton), 2.42 (3H, s, methyl); MS (EI) m/z 363 & 361 ($M^+$, $^{79}$Br & $^{81}$ Br), 264 & 266 ($M^+$—$COCF_3$), 223, 169, 130, 90. Rotations: (R)-(+) $[\alpha]_D^{25}$=+92.6° (C=0.47, MeOH); (S)-(−) $[\alpha]_D^{25}$=−97.8° (C=0.18, MeOH). Anal. ($C_{13}H_{11}BrF_3N_3O$) C, H, N.

To 12 mL fuming nitric acid, cooled to 0° C., was slowly added 500 mg (1.4 mmol) of the bromo derivative with stirring. To the resulting solution was added 1.14 mL of acetic anhydride with continued stirring and cooling. After stirring the reaction mixture at 0° C. for 5 min., the reaction mixture was allowed to come to room temperature and then stirred for 1.5 hr. The completed reaction was poured into 450 mL of ice water and the mixture buffered to pH 7 with NaHCO$_3$. The product was extracted 3× with 50 mL portions of ethyl acetate. The extracts were then dried over $Na_2SO_4$ and solvent removed to afford a yellow residue. Recrystallization from a minimum amount of ethyl acetate, facilitated by the addition of hexane, afforded 8 as light yellow crystals: 466 mg (89%) yield; mp 245–247° C.; TLC (chloroform/methanol [90:10]) $R_f$=0.60; IR (KBr pellet) 3246, 3044, 1741, 1657, 1570, 1538, 1370, 1229, 1159 cm$^{-1}$, $^1$H NMR (CDCl$_3$) δ 10.21 (1H, s, amide NH), 7.38 (1H, s, 8-aromatic proton), 4.75–4.70 (1H, m, 3-methine proton), 4.52–4.42 (1H, m, 1-methylene proton), 4.20–4.12 (1H, m, 1-methylene proton), 3.50–3.40 (1H, m, 2-methylene proton), 2.95–2.85 (1H, m, 2-methylene proton), 2.58 (3H, s, methyl); MS (EI Mode), m/z 406 ($M^+$), 361 ($M^+$—$NO_2$), 309, 293, 280, 263, 189. Rotations: R(+) $[\alpha]_D^{25}$=+70.12° (C=0.42, MeOH); S(−)$[\alpha]_D^{25}$=64.0° (C=0.39, MeOH).

Anal. ($C_{13}H_{10}BrF_3N_4O_3$) C, H, N.

3-Amino-6-bromo-2,3-dihydro-7-methyl-5-nitro-1H-pyrrolo[1,2-a]benzimidazole (9). To a solution of 45 mL of methanol cooled to −70° C. in an isopropanol/dry ice bath was bubbled gaseous ammonia until the volume of liquid doubled. To the resulting solution was added 300 mg (0.737 mmol) of 8 and the mixture was then removed from the dry ice bath and stirred for 48 h at room temperature. The solvent was evaporated and the residue was recrystallized from chloroform/hexane to afford light brown crystals: 151 mg (66%) yield; mp 145–148° C.; TLC (chloroform/methanol [80:20]) $R_f$=0.22; IR (KBr pellet) 3389, 2924, 1532, 1458, 1381, 1294, 878 cm$^{-1}$; $^1$H NMR (CDCl$_3$) δ 7.36 (2H, s, aromatic proton), 4.58 (1H, dd, J=7.9 Hz, J=6.6 Hz, 3-methine proton), 4.29–4.21 and 4.09–4.01 (2H, 2m, 1-methylene protons), 3.15–3.03 and 2.51–2.39 (2H, 2m, 2-methylene), 2.58 (3H, s, 7-methyl); MS (EI mode) m/z 310 and 312 ($M^+$, $^{79}$Br & $^{81}$Br), 293 and 295 ($M^+$, —$NH_3$), 263 and 265 ($M^+$—$NH_3$—NO). Rotations: R(−) $[\alpha]_D^{25}$=−8.1° (C=0.42, MeOH); S(+)$[\alpha]_D^{25}$==10.1° (C=0.16, MeOH).

Anal. ($C_{11}H_{11}N_4O_2 \cdot 0.25H_2O$) C, H, N.

3-Amino-6-azindinyl-2,3-dihydro-7-methyl-1H-pyrrolo[1,2-a]benzimidazole-5,8-dione(2) A solution consisting of 70 mg (0.225 mmol) of 9, 70 mg of 5% Pd on charcoal, and 70 mL of methanol was shaken under 50 psi $H_2$ for 24 h. The reaction mixture was filtered through Celite, evaporated to dryness, and then combined with a solution of 0.333 g $KH_2PO_4$ in a 30 mL of water. The resulting solution was combined with another solution consisting of 1.0 g of $KH_2PO_4$ and 0.700 g Fremy salt in 50 mL of water. The reaction mixture was stirred at room temperature for 6 h and then concentrated under high vacuum to a residue, which was placed on a 25 mL Baker Bond Phenyl reverse phase column prepared with 100% water. The unstable aminoquinone was eluted from the column with water and the combined fractions were concentrated to a dry residue, which was dissolved in 10 mL of methanol and 0.3 mL of azirindine. This reaction mixture was stirred at room temperature for 5 h. The solvent was evaporated and the residue was purified by flash column chromatography employing chloroform/methanol [95:5] as the eluent. The product fractions were evaporated to dryness and the residue recrystallized from chloroform/hexane to afford 2 as a red solid: 6.0 mg (10.3%) overall yield; mp>240° C., dec; TLC (chloroform/methanol [80:20]) $R_f$=0.17; IR (KBr pellet) 3387, 2996, 2924, 1674, 1632, 1576, 1518, 1377, 1341, 1312, 1140, 988, cm$^{-1}$; $^1$HNMR (DMSO-d$_6$) δ 4.23–4.15 and 4.06–3.97 (3H, 2m, 3-methine and 1-methylene), 2.89–2.78 and 2.27–2.16 (2H, 2m, 2-methylene), 2.29 (4H, s, aziridinyl protons), 1.94 (3H, s, 7-methyl); MS (EI mode) m/z 258 (M$^+$), 240, 214. Anal. (C$_{13}$H$_{14}$N$_4$O$_2$.0.35H$_2$O) C, H, N.

6-Bromo-3-Carbamido-2,3-dihydro-7-methyl-5-nitro-1H-pyrrolo[1,2-a]benzimidazole(10) was prepared by the following two-step procedure starting with 9.

A solution of 150 mg (0.482 mmol) 9 in 9 mL of dry pyridine was cooled to 0° C. in an ice bath. To the cooled solution was added 0.3 mL of phenylchloroformate and the reaction mixture was stirred at 0° C. for 15 min. The mixture was then removed from the ice bath and allowed to warm to room temperature with stirring over 1 h. The reaction mixture was diluted with 50 mL of ethyl acetate and the resulting mixture washed 3× with 15 mL of 20% aqueous acetic acid, 2× with 10 mL portions of 0.12N aqueous hydrochloric acid, and finally 2× with 15 mL of water. The ethyl acetate layer was dried over Na$_2$SO$_4$ and the solvent was evaporated to a residue, which was recrystallized from chloroform/hexane to afford the phenoxyamido derivative as a light brown solid: 162 mg (78%) yield; mp 175–178° C.; TLC (chloroform/methanol [80:20]) $R_f$=0.66; IR (KBr pellet) 3306, 1736, 1537, 1491, 1208 cm$^{-1}$; $^1$H NMR (DMSO-d$_6$) δ 8.55 (1H, d, J=9 Hz, amide proton), 7.87 (1H, s, C(8) proton), 7.4–6.7 (5H, 3m, aromatic protons), 5.28 (1H, q, J=6.6 Hz, 3-methine), 4.36–4.26 and 4.18–4.09 (2H, 2m, 1-methylene), 3.13–3.01 and 2.61–2.49 (2H, 2m, 2-methylene), 2.54 (3H, s, 7-methyl); MS (EI mode) m/z 430 and 432 (M$^+$, $^{79}$Br & $^{81}$Br). Rotations: R(−) [α]$_D$$^{25}$=+13.6° (C=0.26, MeOH); S(+)[α]$_D$$^{25}$==−14.0° (C=0.33, MeOH).

Anal. (C$_{18}$H$_{15}$BrN$_4$O$_4$.0.25 H$_2$O) C, H, N.

Gaseous ammonia was passed into a dry flask cooled to −70° C. with isopropanol/dry ice bath until 20 mL of liquid ammonia was obtained. A solution of 150 mg (0.348 mmol) of the phenoxyamido derivative in 10 mL of dry methylene chloride was added to the liquid ammonia and the resulting mixture was stirred for 30 min at −70° C. The reaction mixture was then removed from the dry ice bath and stirred for 3 h at room temperature. The solvent was evaporated and the solid residue was recrystallized from chloroform/hexane to afford 10 as an off-white solid: 104 mg (84.5%) yield; mp 240–241° C.; TLC (chloroform/methanol [80:20]) $R_f$=0.34, IR (KBr pellet) 3410, 3293, 2922, 1657, 1588, 1532, 1371, cm$^{-1}$; $^1$H NMR (DMSO d$_6$) δ 7.83 (1H, d, J=1.2 Hz, aromatic proton), 6.69 (1H, d, J=8.4 Hz, amide protons), 5.69 (2H, s, amide protons), 5.22 (1H, m, 3-methine), 4.30–4.21 and 4.11–4.03 (2H, 2m, 1-methylene), 2.99–2.88 and 2.41–2.30(2H, 2m, 2-methylene), 2.54 (3H, s, 7-methyl); MS (EI mode) m/z 353 and 355 (M$^+$, $^{79}$Br & $^{81}$Br). Anal (C$_{12}$H$_{12}$N$_5$O$_3$.0.5H$_2$O) C, H, N.

3-Carbamido-6-aziridinyl-2,3-dihydro-7-methyl-1H-pyrrolo[1,2-a]benzimidazole-5,8-dione(3) was prepared from 10 by the following two-step procedure. A solution of 120 mg (0.339 mmol) of 10, 80 mg of 5% Pd on charcoal, and 200 mL of methanol was shaken under 50 psi H for 15 h. The reaction mixture was filtered through Celite and the solvent was removed by evaporation. The residue was dissolved into a solution of 296 mg of KH$_2$PO$_4$ in 120 mL of water. To this solution was added a Fremy salt solution consisting of 1.2 g of Fremy salt and 1.8 g KH$_2$PO$_4$ in 174 mL of water. The reaction was stirred at room temperature for 1.5 h and then concentrated with high vacuum. The residue was placed on a 25 mL Bakerbond Phenyl reverse phase column prepared with 100% water. The yellow product fractions were collected from the column employing water as the eluent. The fractions were evaporated to dryness and the residue recrystallized from ethyl acetate/hexane: 46 mg (52%) yield; mp 180–183° C. TLC (chloroform/methanol [80:20]) $R_f$=0.48; IR (KBr pellet) 3393, 3297, 3212, 1659, 1593, 1570, 1516, 1329, 1152 cm$^{-1}$; $^1$HNMR (DMSO-d$_6$) δ 6.64 (1H, d, J=8.4 Hz, amide proton), 6.57 (1H, d, J=2.1 Hz, aromatic proton), 5.67 (2H, s, amine protons), 5.09–5.01 (1H, m, 3-methine), 4.29–4.21 and 4.14–4.06 (2H, 2m, 1 methylene), 2.99–2.88 and 2.41–230 (2H, 2m, 2 methylene), 2.01 (3H, d, J=1.5 Hz, 7-methyl); MS (EI mode) m/z 260 (M+), 243 (M$^+$—NH$_3$), 217 (M$^+$—H—N=C=O). Anal (C$_{12}$H$_{12}$N$_4$O$_3$.0.35H$_2$O) C, H, N.

A solution of 20 mg (0.077 mmol) of the carbamide quinone, 10 mL of dry methanol, and 0.3 mL of aziridine were stirred at room temperature for 3 h. The reaction solvent was evaporated and the red residue was dissolved into a 9:1 chloroform/methanol mixture and purified by flash column chromatography using 9:1 chloroform/methanol as the eluent. Evaporation of the solvent gave a red solid which was recrystallized from chloroform/hexane: 8.1 mg (35.0%) yield; mp 200–205° C.; TLC (chloroform/methanol [80:20]) $R_f$=0.37; IR (KBr pellet) 3351, 1678, 1647, 1522, 1316, cm$^{-1}$; $^1$H NMR (DMSO-d$_6$)δ 6.62 (1H, d, J=7.8 Hz, amide proton), 5.65 (2H, s, amine protons), 5.04–4.96 (1H, m, 3-methine), 4.25–4.17 and 4.10–4.01 (2H, 2m, 1-methylene), 2.97–2.86 and 2.39–2.30 (2H, 2m, 2-methylene), 2.30 (4H, s, aziridinyl protons), 1.95 (3H, s, 7-methyl); MS (EI mode) m/z 301 (M$^+$). Anal. (C$_{14}$H$_{15}$N$_5$O$_3$.1.0H$_2$O): C, H, N.

Alkylation of DNA by Reduced PBIs. To a mixture of 1–2 mg of DNA (poly[dA]. poly[dT], poly[dG]. poly[dC], poly [dA-dT]. poly[dT-dA]) in 2.0 mL of 0.05 M of pH 7.4 tris buffer and 2 mg of Pd on carbon was added a five-to-one base pair equivalent amount of the PBI dissolved in 0.5 mL of dimethylsulfoxide. The resulting solution was degassed under argon for 30 min., after which the mixture was purged with H$_2$ for 10 min. The solution was then purged with argon for 10 min. and the placed in a 30° C. bath for 24 h. The reaction was opened to the air and the catalyst was removed with a Millex-PF 0.8 μM syringe filter. The filtrate was adjusted to 0.3M acetate with a 3M stock solution of pH 5.1 acetate and the diluted with two volumes of ethanol. The mixture was chilled at −20° C. for 12 h and the DNA pellet collected by centrifuging at 12,000 g for 20 min. The pellet was redissolved in water and then precipitated and centrifuged again. The resulting pellet was suspended in ethanol, centrifuged, and dried.

DT-Diaphorase Reduction Kinetics Studies. Kinetic studies were carried out in 0.05 M pH 7.4 tris.HCl buffer, under anaerobic conditions, employing Thunberg cuvettes. A 2 mM stock solution of the appropriate PBI or APBI was prepared in dimethyl sulfoxide (DMSO). To the top port was added the quinone stock and to the bottom port was added DT-diaphorase and NADH in the tris buffer. The top and bottom ports were purged with argon for 20 minutes and equilibrated to 30° C. The ports were then mixed and the reaction followed at 296 nm for 25 minutes to obtain initial rates. The concentrations upon after mixing were 0.3 mM NADH, 1 to 20×10-5 M quinone, and 14.5 nM (based on flavin) of enzyme active sites. The value of Δε was calculated from the initial and final absorbance values for complete quinone reduction, usual value for Δε is 6000 to 8000 M−1 cm−1. The value of Δε was used to calculate Vmax in M sec−1. The results were fitted to a Lineweaver-Burke plot from which kcat/Km values were calculated based on 14.5 nM of active sites.

SCHEME C

Percentages of PBI Incorporation into Various DNAs

| DNA | S(−)-A | R(+)-A | S(−)-B | R(+)-B | S(−)-C | R(+)-C |
|---|---|---|---|---|---|---|
| Poly [dG] | | | | | | |
| Poly [dC] | 6.6 | 9.9 | 52 | 105 | 12.4 | 17 |
| Poly [dA] | | | | | | |
| Poly [dT] | 17.4 | 101 | 186 | 60 | 70 | 31 |

SCHEME D

Parameters for DT-diaphorase Substrate Activity and Melanoma an Ovarian Cancer Log $_{10}$LC$_{50}$ (Moles/liter) Values for APBI Analogues

| PBI | $K_m \times 10^5$ | $V_{max}$ (nM sec-1) | $K_{cat}/K_m \times 10^{-4}$ |
|---|---|---|---|
| S(−)-A | 12.7 | 47.6 | 3.74 |
| R(+)-A | 3.8 | 28 | 7.5 |
| S(−)-B | | | |
| R(+)-B | 2.4 | 14.6 | 6.1 |
| S(−)-C | 5.15 | 21.8 | 4.23 |
| R(+)-C | 4.6 | 39.3 | 8.59 | for localized use about the cut is, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an eatable carbohydrate material, such as lactose or starch, advantageously, a sweetening agent or sugar is present as well as a flovoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into Elemental Analysis

| | | Calculated | | | Found | | |
|---|---|---|---|---|---|---|---|
| Compound # | (Formula) | C % | H % | N % | C % | H % | N % |
| S(−)7 | $C_{13}H_{12}F_3N_3O$ | 55.12 | 4.27 | 14.83 | 55.01 | 4.24 | 14.70 |
| R(+)7 | | | | | | | |
| 6-Bromo 7 | $C_{13}H_{11}BrF_3N_3O$ | 43.11 | 3.06 | 11.60 | 44.03 | 3.20 | 11.44 |
| 8 | $C_{13}H_{10}BrF_3N_4O_3$ | 38.35 | 2.48 | 13.76 | 39.42 | 2.88 | 13.22 |
| 9 | $C_{11}H_{11}N_4O_2$ 0.25 $H_2O$ | 41.85 | 3.67 | 17.75 | 42.05 | 3.54 | 17.48 |
| 2 | $C_{18}H_{15}N_4O_4$ 0.35 $H_2O$ | 59.16 | 5.48 | 21.23 | 59.55 | 5.54 | 20.30 |
| 3-Phenoxy amido-9 | $C_{18}H_{15}BrN_4O_4$ 0.25 $H_2O$ | 49.61 | 3.59 | 12.86 | 49.66 | 3.53 | 12.48 |
| 10 | $C_{12}H_{12}N_4O_3$ 0.35 $H_2O$ | 54.21 | 4.68 | 21.07 | 54.22 | 4.69 | 20.57 |
| 3 | $C_{14}H_{15}N_5O_3$ 1.0 $H_2O$ | 67.71 | 8.12 | 11.28 | 67.77 | 8.14 | 11.37 |

Dosing

The dosage administered will be dependent upon the identity of the neoplastic disease; the types of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies my means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oil administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either cyclopent(b) indole 3b–e and/or indole 2a–c, and/or indole 1a–c or any other compound described herein.

Composition "A"

Hard-Gelatin Capsules

One thousand two-piece hard gelatin capsules for oral use, each capsule containing 200 mg of an active ingredient are prepared from the following types and amounts of ingredients:

| Active ingredient, micronized | 200 g |
|---|---|
| Corn Starch | 20 g |
| Talc | 20 g |
| Magnesium stearate | 2 g |

Active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient are prepared from the following types and amounts of ingredients:

| Active ingredient, micronized | 200 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients.

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

The sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. | 1000 ml. |

All ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. | 1000 ml. |

All ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition "J"

Insufflation

One hundred grams of an active ingredient in bulk form is finely divided by means of an air micronizer.

The foregoing composition is useful for treating antineoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

What is claimed is:

1. A pharmaceutical preparation for administration to an animal or human subject, for treating neoplastic disease in the subject, comprising a compound having a structure as follows:

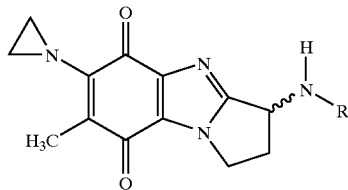

wherein R is selected from the group consisting of H or $CONH_2$,
and a pharmaceutically acceptable carrier therefor.

2. The preparation of claim 1, wherein R is H.
3. The preparation of claim 1, wherein R is $CONH_2$.
4. A compound having the following structure:

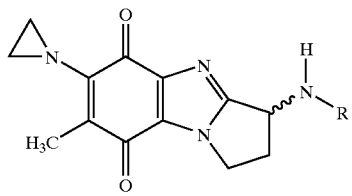

wherein R is selected from the group consisting of H and $CONH_2$.

5. The compound of claim 4, wherein R is H.
6. The compound of claim 4, wherein R is $CONH_2$.
7. A method for treating cancer, comprising administering to an animal or human subject afflicted with cancer comprising cancer cells containing DT-diaphorase, an amount sufficient to inhibit said cancer of a compound having a structure as follows:

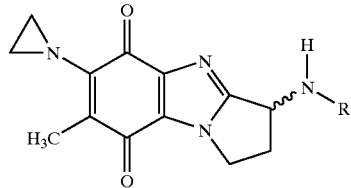

wherein R is selected from the group consisting of H and $CONH_2$.

8. The method of claim 7, wherein R is H.
9. The method of claim 7, wherein R is $CONH_2$.
10. A method for treating cancer selected from the group consisting of melanoma, central nervous system cancer, colon cancer, ovarian cancer and lung cancer, comprising administering to an animal or human subject in need thereof an amount sufficient to inhibit said cancer of a compound having a structure as follows:

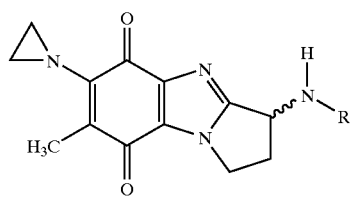

wherein R is selected from the group consisting of H, $CONH_2$ and $COCH_3$.

* * * * *

UNITED STATES PATENT AND TRADEMARK OFFICE
CERTIFICATE OF CORRECTION

PATENT NO. : 6,998,413 B1
APPLICATION NO. : 09/889530
DATED : February 14, 2006
INVENTOR(S) : Edward B. Skibo It is certified that error appears in the above-identified patent and that said Letters Patent is hereby corrected as shown below:

- In Claim 1, at column 19, line 24, the text "neoplastic disease" should be changed to --cancer --;

- at column 19, line 25, the text "a compound" should be changed to --an effective amount of a compound --;

- at column 19, lines 35-36, "H or $CONH_2$" should be changed to -- H and $CONH_2$--.

Signed and Sealed this

Twenty-second Day of August, 2006

JON W. DUDAS
*Director of the United States Patent and Trademark Office*